(12) United States Patent
Igarashi

(10) Patent No.: US 12,263,284 B2
(45) Date of Patent: Apr. 1, 2025

(54) FLOW PATH DEVICE AND BIOLOGICAL COMPONENT BAG SYSTEM

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 555 days.

(21) Appl. No.: 17/629,284

(22) PCT Filed: Jul. 17, 2020

(86) PCT No.: PCT/JP2020/027771
§ 371 (c)(1),
(2) Date: Jan. 21, 2022

(87) PCT Pub. No.: WO2021/015111
PCT Pub. Date: Jan. 28, 2021

(65) Prior Publication Data
US 2022/0241471 A1    Aug. 4, 2022

(30) Foreign Application Priority Data

Jul. 22, 2019  (JP) ................................. 2019-134560

(51) Int. Cl.
*A61M 1/02*    (2006.01)
(52) U.S. Cl.
CPC .......... *A61M 1/0222* (2014.02); *A61M 1/029* (2013.01); *A61M 1/0218* (2014.02); *A61M 2202/0427* (2013.01)

(58) Field of Classification Search
CPC .......... A61M 1/029; A61M 2202/0427; A61M 1/0209; A61M 1/0218; A61J 1/05; A61J 1/10
See application file for complete search history.

(56) References Cited

U.S. PATENT DOCUMENTS 7,041,076 B1 *  5/2006  Westberg ............ A61M 60/427
                                                        604/4.01
2007/0278155 A1  12/2007  Lo et al.
2009/0194489 A1   8/2009  Vandlik et al.

FOREIGN PATENT DOCUMENTS

JP    2005-534346    11/2005
JP    2010-502405     1/2010
JP    2012-510298     5/2012
(Continued)

OTHER PUBLICATIONS

International Search Report prepared by the European Patent Office for International (PCT) Patent Application No. PCT/JP2020/027771, dated Jan. 29, 2021, 7 pages.
(Continued)

*Primary Examiner* — Terry K Cecil
(74) *Attorney, Agent, or Firm* — Sheridan Ross P.C.

(57) ABSTRACT

A flow path device of a biological component bag system is equipped with a device main body. The device main body includes a first sheet and a second sheet, and flow paths are formed between the first sheet and the second sheet. The flow paths include a first flow path, a second flow path, a filter accommodating chamber, and a third flow path. In the device main body, flow path sealed portions that join the first sheet and the second sheet to each other in a liquid-tight manner are disposed along the flow paths.

18 Claims, 13 Drawing Sheets

(56) References Cited

FOREIGN PATENT DOCUMENTS

| WO | WO 2010/061863 | 6/2010 |
|----|----------------|--------|
| WO | WO 2018/051982 | 3/2018 |
| WO | WO 2018/062211 | 4/2018 |
| WO | WO 2019/065813 | 4/2019 |

OTHER PUBLICATIONS

Written Opinion prepared by the European Patent Office for International (PCT) Patent Application No. PCT/JP2020/027771, dated Jan. 29, 2021, 11 pages.
Official Action (with English translation) for Japan Patent Application No. 2022-502438, dated Dec. 5, 2023, 10 pages.
International Preliminary Report on Patentability for International (PCT) Patent Application No. PCT/JP2020/027771, dated Jan. 25, 2022, 13 pages.
Official Action for European Patent Application No. 20749974.0, dated Dec. 4, 2024, 7 pages.
Official Action for European Patent Application No. 20749974.0, dated Jan. 24, 2025, 5 pages.

\* cited by examiner

[Fig. 7]
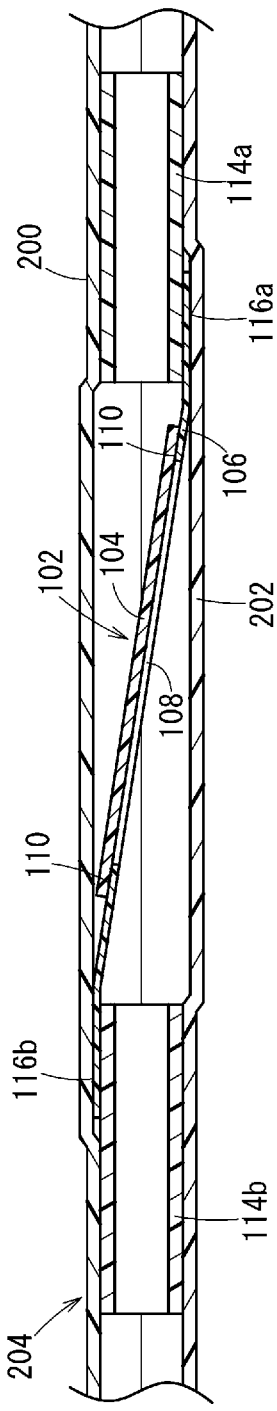
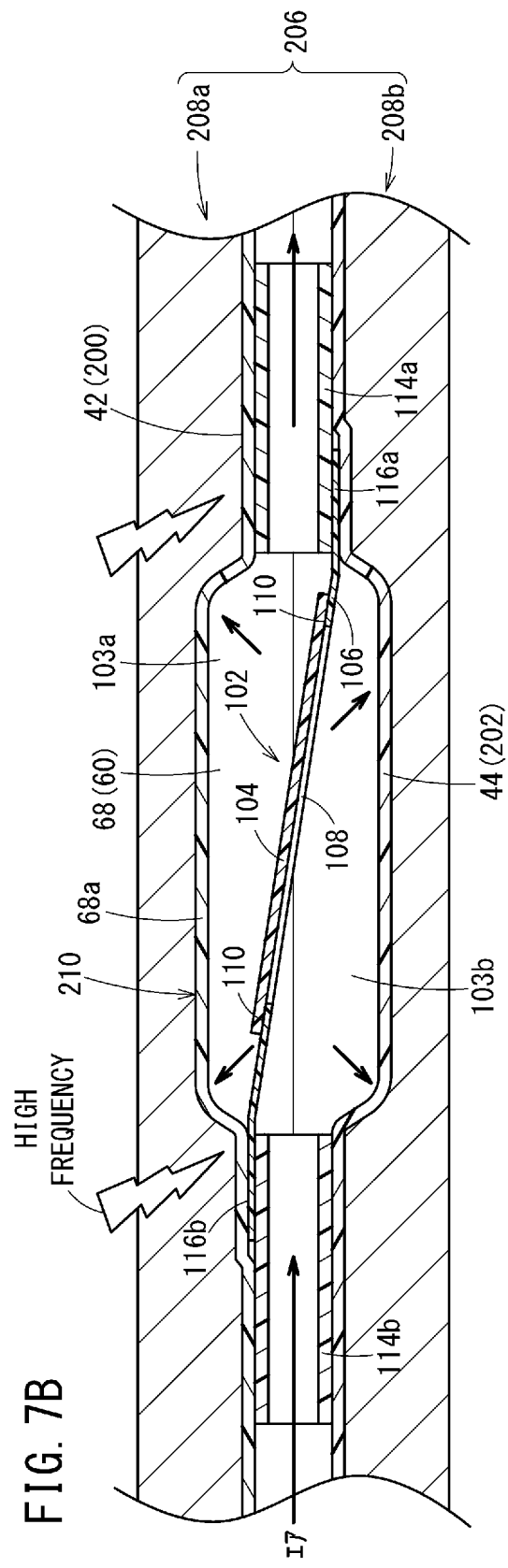

[Fig. 8]
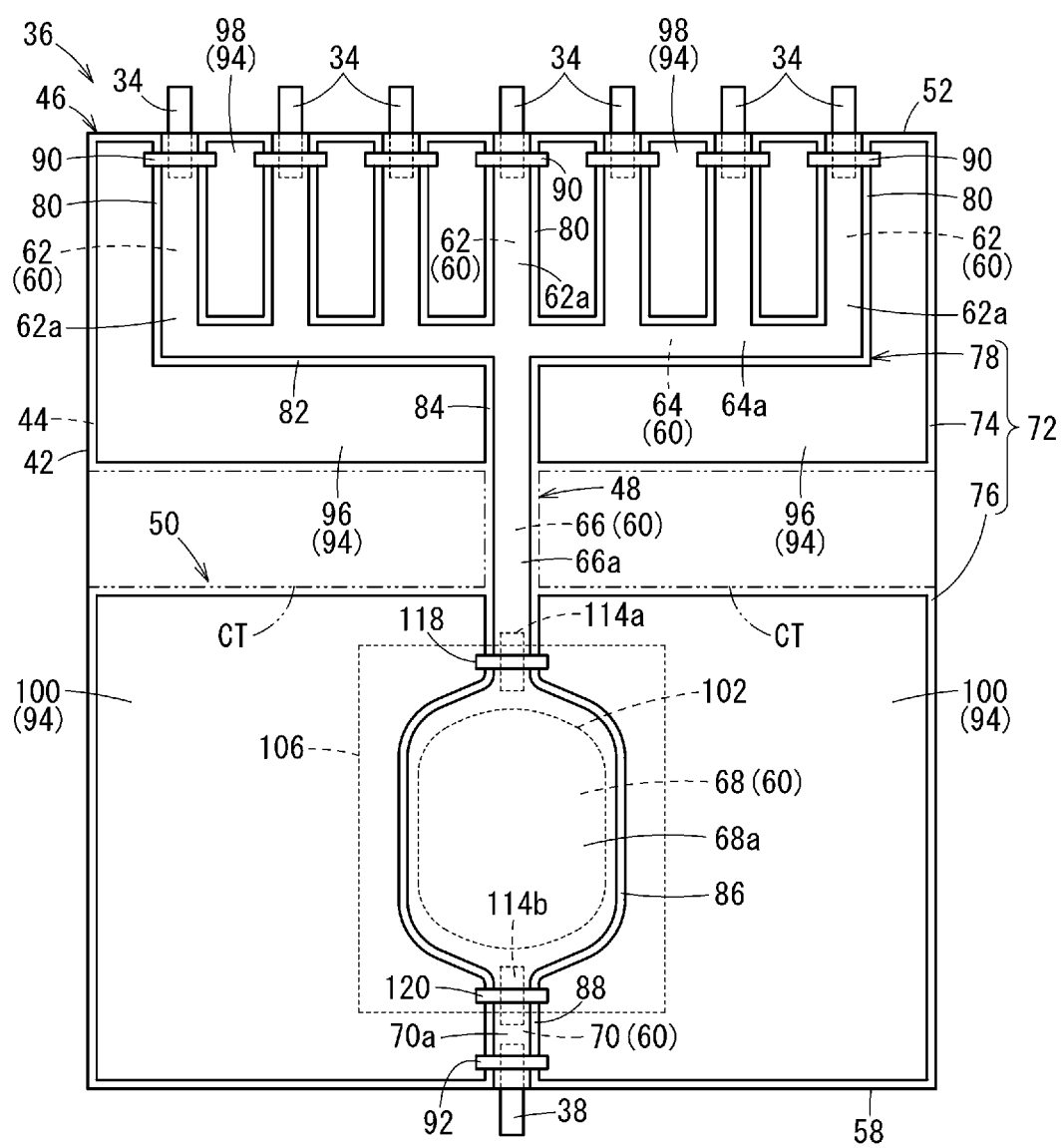

[Fig. 11]
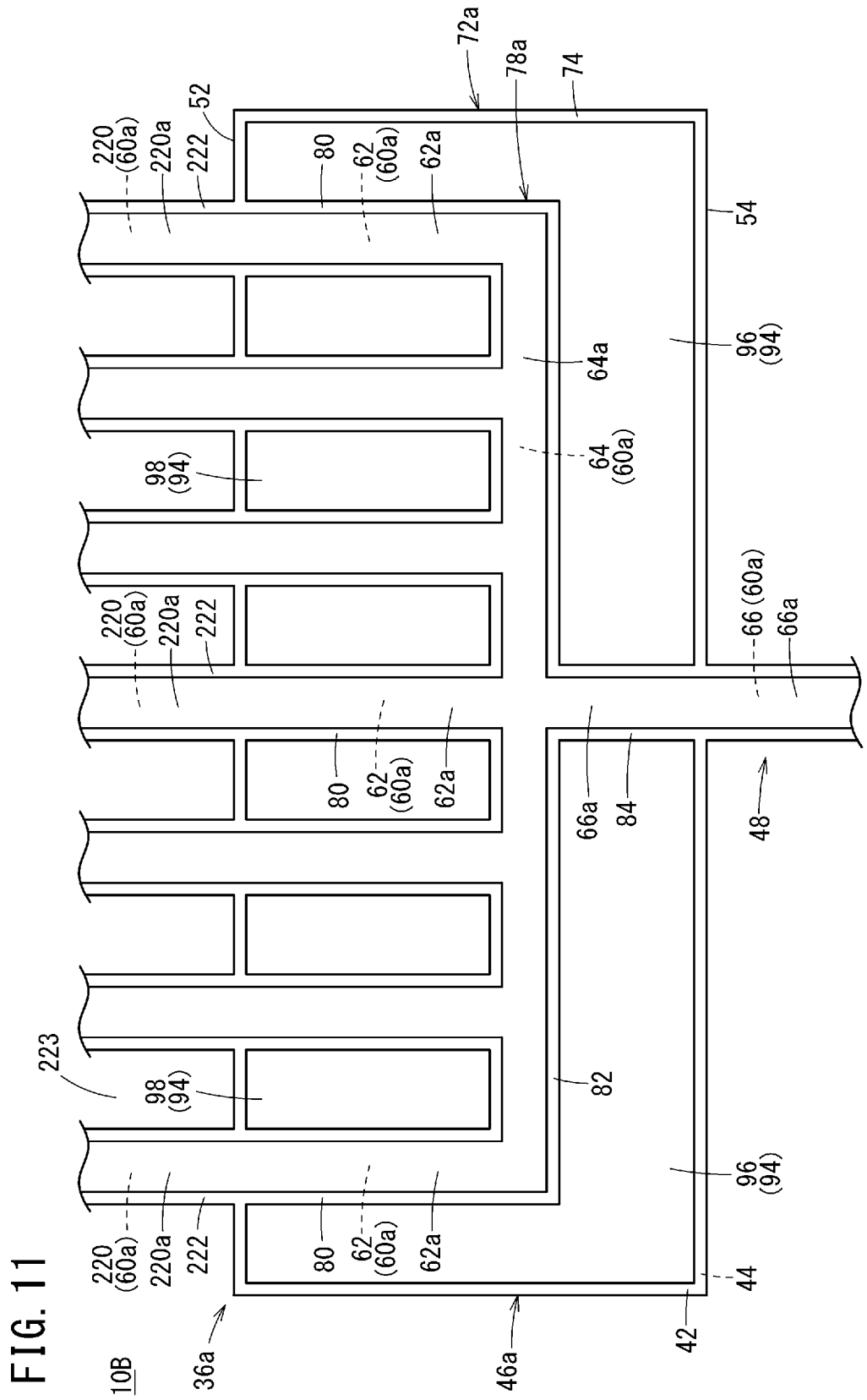

[Fig. 12]
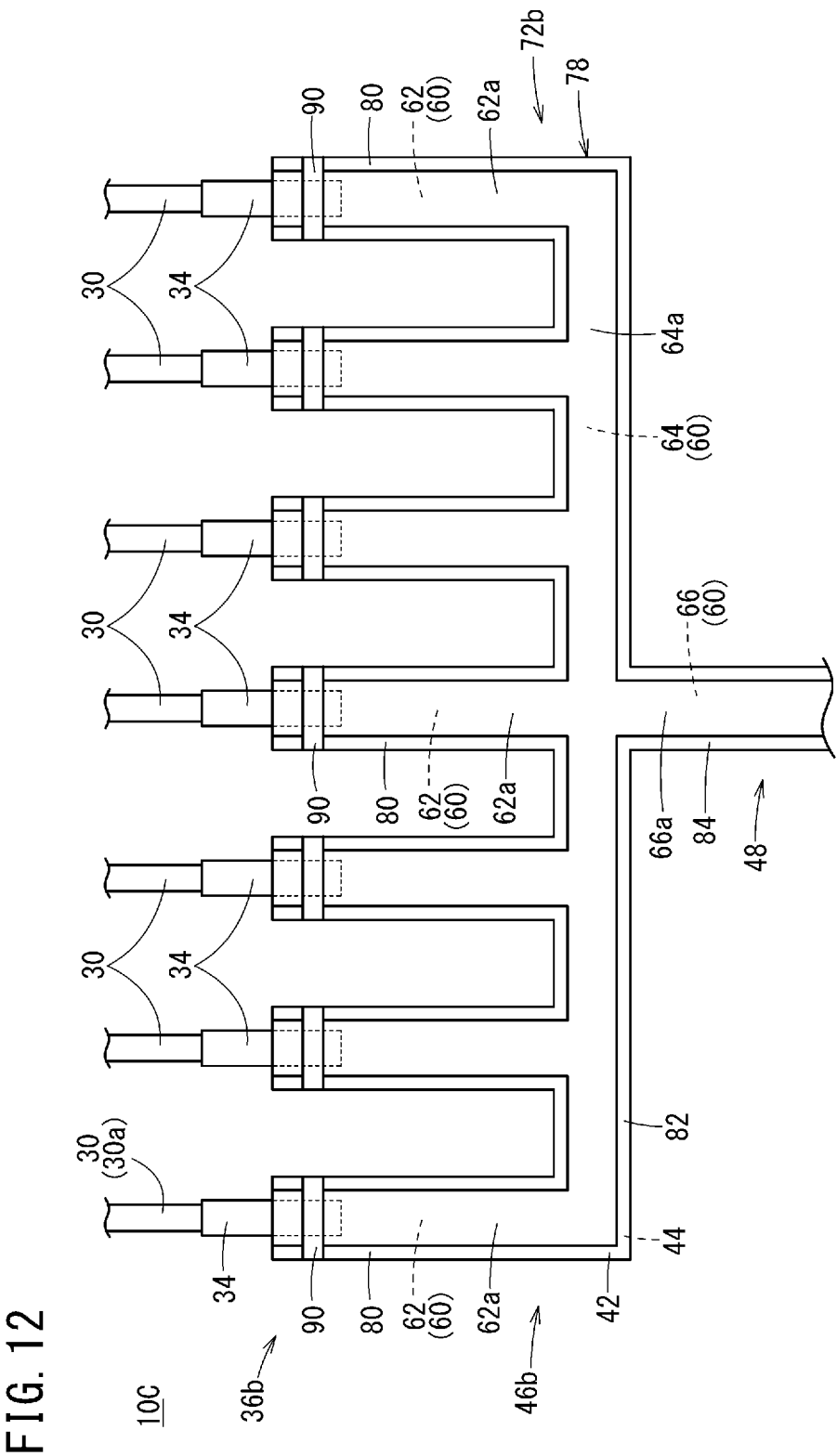

[Fig. 13]
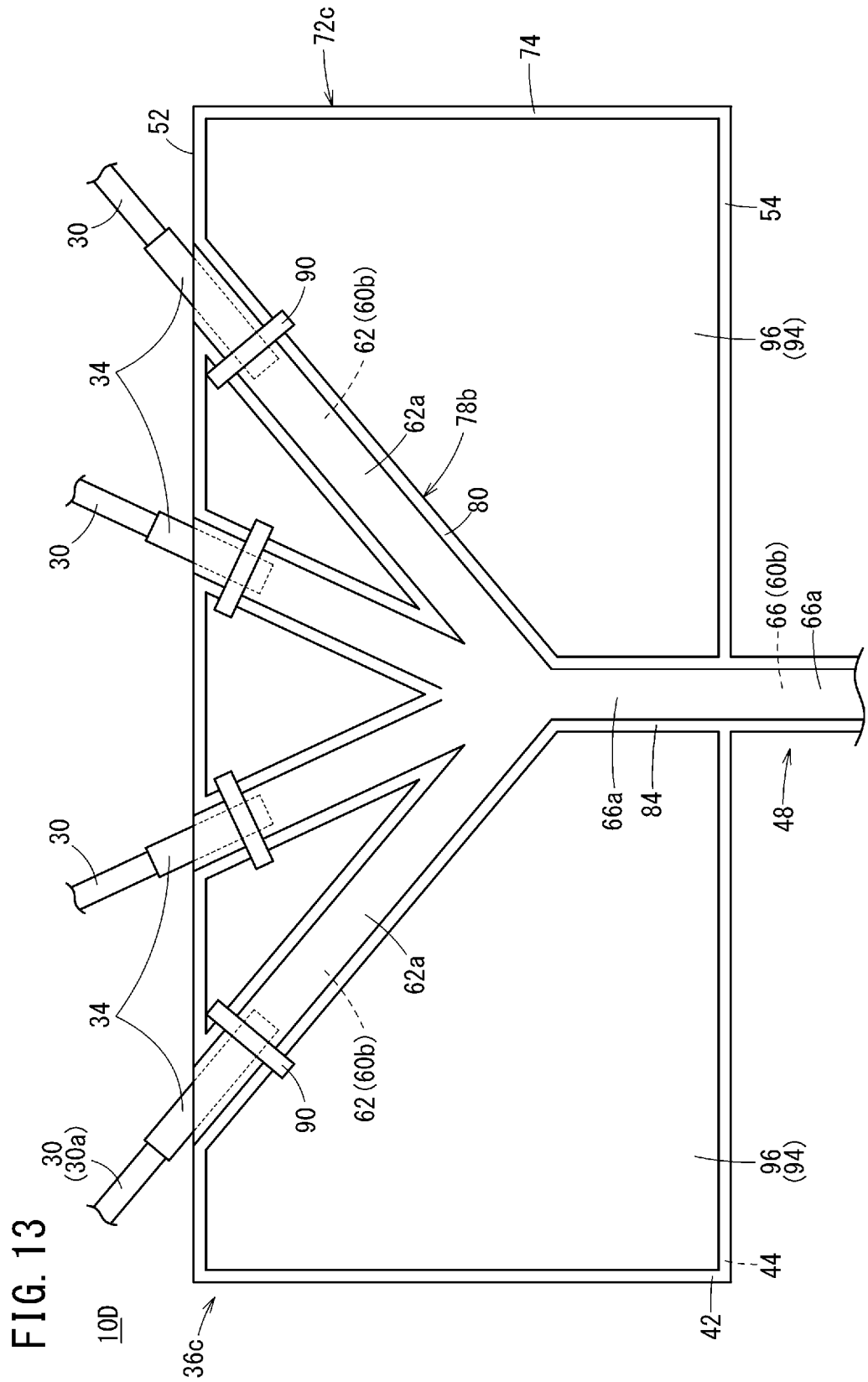

FLOW PATH DEVICE AND BIOLOGICAL COMPONENT BAG SYSTEM

CROSS REFERENCE TO RELATED APPLICATIONS

This application is a national stage application under 35 U.S.C. 371 and claims the benefit of PCT Application No. PCT/JP2020/027771 having an international filing date of 17 Jul. 2020, which designated the United States, which PCT application claimed the benefit of Japanese Patent Application No. 2019-134560 filed 22 Jul. 2019, the entire disclosures of each of which are hereby incorporated herein by reference, in their entireties, for all that they teach and for all purposes.

TECHNICAL FIELD

The present invention relates to a flow path device and a biological component bag system.

BACKGROUND ART

In FIG. 9 of International Publication No. WO 2018/062211, a blood platelet bag system is disclosed in which a buffy coat accommodated in a plurality of bags is transferred and collected in a single pooling bag via a flow path device, and thereafter, leukocytes are removed by a filter to thereby obtain blood platelets. Such a flow path device includes a plurality of branch connectors constituted by a hard material, and a plurality of tubes connected to a plurality of port members of the respective branch connectors. Further, the filter is connected to the pooling bag via a tube.

SUMMARY OF INVENTION

In the above-described flow path device, the plurality of branch connectors and the plurality of tubes are required, and therefore, the number of component parts is relatively large. Further, in the above-described blood platelet bag system, since a large number of component parts (branch connectors, tubes, and the filter) must be joined together, the joining steps become relatively large in number. Therefore, there is a concern that the cost of the flow path device and the blood platelet bag system (biological component bag system) may increase.

The present invention has been devised taking into consideration the aforementioned problems, and has the object of providing a flow path device and a biological component bag system which are capable of achieving a reduction in cost.

One aspect of the present invention is characterized by a flow path device in which there are formed flow paths configured to allow at least one liquid of a biological fluid and a medicinal solution to flow therethrough, the flow path device including a device main body in which the flow paths are formed, the device main body including a first sheet formed by a soft material, and a second sheet formed by a soft material and that is superimposed on the first sheet, wherein the flow paths are formed between the first sheet and the second sheet, the flow paths including a plurality of first flow paths, a single second flow path configured to communicate with the plurality of first flow paths, a filter accommodating chamber provided in the second flow path and in which there is accommodated a filter member configured to remove a predetermined biological component in the biological fluid, and a third flow path through which the liquid having passed through the filter accommodating chamber flows, wherein flow path sealed portions, which are configured to join the first sheet and the second sheet to each other in a liquid-tight manner, are provided in the device main body.

Another aspect of the present invention is characterized by a flow path device in which there are formed flow paths configured to allow at least one liquid of a biological fluid and a medicinal solution to flow therethrough, the flow path device including a device main body in which there are provided sealed portions configured to mutually join a plurality of sheets formed by a soft material in a liquid-tight manner to thereby form the flow paths in the interior of the sheets, wherein the device main body is made up from a first main body portion, a second main body portion, and a connecting part configured to connect the first main body portion and the second main body portion, the first main body portion including a plurality of first flow paths, and a second flow path in communication with the plurality of first flow paths, the second main body portion including a filter accommodating chamber provided in the second flow path and in which there is accommodated a filter member configured to remove a predetermined biological component in the biological fluid, and a third flow path through which the liquid having passed through the filter accommodating chamber flows, wherein the connecting part forms at least a portion of the second flow path.

Yet another aspect of the present invention is characterized by a biological component bag system configured to collect a desired biological component from a biological fluid, the biological component bag system including a plurality of first bags in which the biological fluid is accommodated, a flow path device to which the plurality of first bags are connected, and a second bag configured to accommodate the biological component which is guided from the plurality of first bags via the flow path device, wherein the flow path device includes a device main body in which there are formed flow paths configured to allow at least one liquid of the biological fluid and a medicinal solution to flow therethrough, the device main body including a first sheet formed by a soft material, and a second sheet formed by a soft material and that is superimposed on the first sheet, wherein the flow paths are formed between the first sheet and the second sheet, the flow paths including a plurality of first flow paths, a second flow path configured to communicate with the plurality of first flow paths, a filter accommodating chamber provided in the second flow path and in which there is accommodated a filter member configured to remove a predetermined biological component in the biological fluid, and a third flow path through which the liquid having passed through the filter accommodating chamber flows, wherein flow path sealed portions, which are configured to join the first sheet and the second sheet to each other in a liquid-tight manner, are provided in the device main body.

According to the present invention, the flow paths (the plurality of first flow paths, the second flow path, the filter accommodating chamber, and the third flow path) are formed between the first sheet and the second sheet. Therefore, compared to a conventional product in which a plurality of branch connectors and a plurality of tubes are used, the number of component parts of the flow path device can be reduced. Thus, a reduction in costs can be achieved.

Further, in accordance with the flow path device and the biological component bag system according to the aspects of the present invention, the flow path sealed portions are provided along the flow paths. Consequently, in the flow path device, since there is no need to join a large number of component parts, the number of joining steps can be reduced.

BRIEF DESCRIPTION OF DRAWINGS

FIG. 7A is an explanatory diagram of a joining step shown in FIG. 4A, and FIG. 7B is an explanatory diagram of a blow molding step shown in FIG. 4A;

FIG. 8 is an explanatory diagram of a trimming step shown in FIG. 4A;

FIG. 11 is a partially enlarged plan view of a flow path device according to a first modification;

FIG. 12 is a partially enlarged plan view of a flow path device according to a second modification; and FIG. 13 is a partially enlarged plan view of a flow path device according to a third modification.

DESCRIPTION OF EMBODIMENTS

Hereinafter, preferred embodiments of a flow path device and a biological component bag system according to the present invention will be presented and described in detail below with reference to the accompanying drawings.

Figure 1:
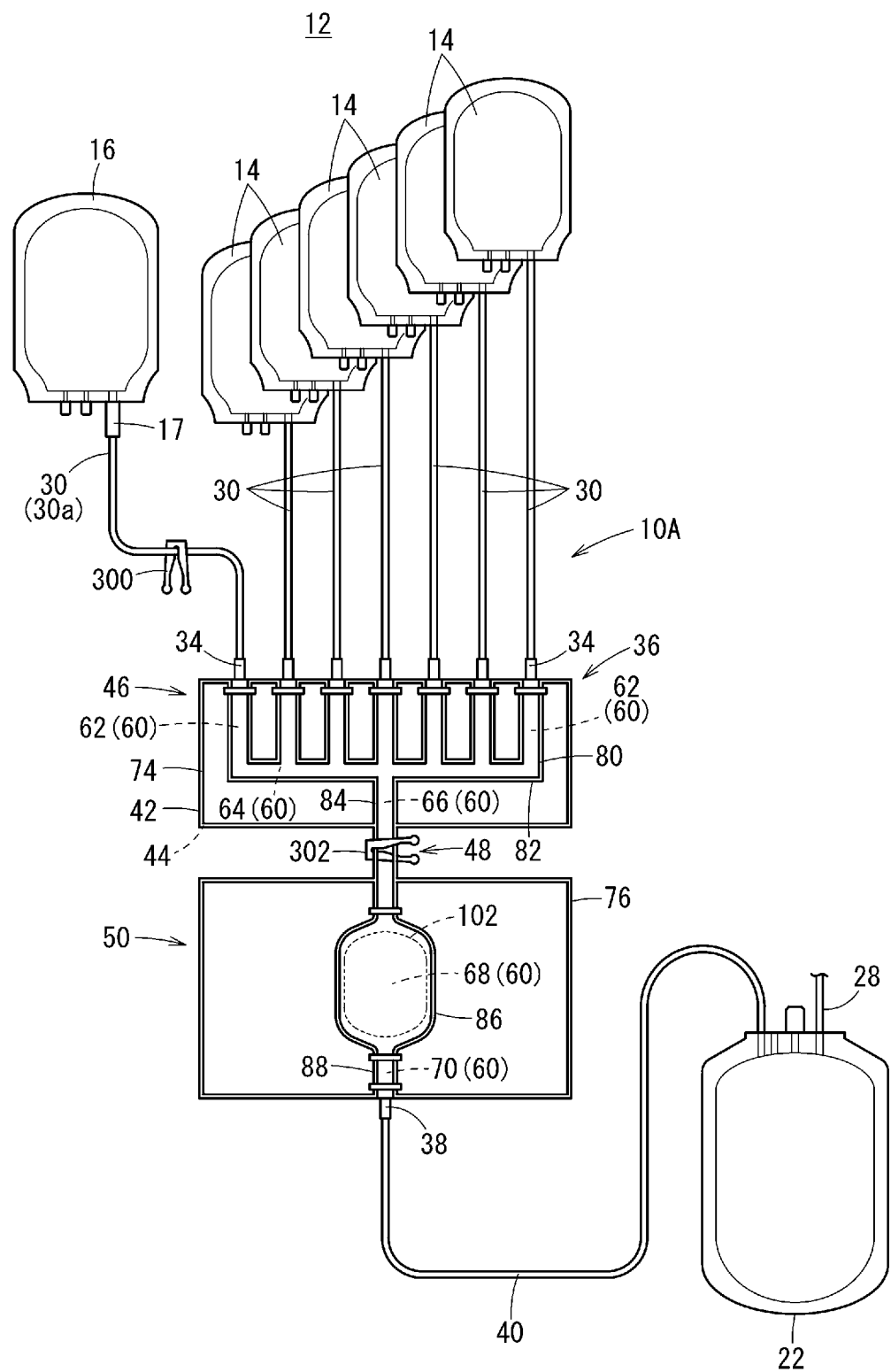
FIG. 1 is a schematic configuration diagram of a biological component bag system equipped with a flow path device according to an embodiment of the present invention.

As shown in FIG. 1, the biological component bag system 12 according to one embodiment of the present invention is a system that removes leukocytes from a buffy coat accommodated in a plurality of BC bags 14 in order to obtain blood platelets (a blood platelet product). However, the biological component bag system 12 is not limited to such an example in which blood platelets are collected from a buffy coat, and may be any system that serves to collect a desired biological component from a biological fluid.

The biological component bag system 12 includes the plurality of BC bags 14 (first bags), a medicinal solution bag 16, a flow path device 10A, and a blood platelet bag 22 (second bag).

The BC bags 14 are constituted in bag shapes, for example, by overlapping sheet materials possessing flexibility and made of a soft resin such as polyvinyl chloride, polyolefin, or the like, and then fusion bonding (heat fusion bonding, high frequency fusion bonding) or adhering the sheet materials to each other at sealed portions on peripheral edges thereof. Moreover, the medicinal solution bag 16 and the blood platelet bag 22 are configured in the same bag shape as the BC bags 14.

The BC bags 14 contain the buffy coat. The buffy coat inside the BC bags 14 is obtained, for example, by centrifuging blood (whole blood) containing a plurality of blood components into blood plasma, the buffy coat, and concentrated red blood cells. However, the method of collecting the buffy coat is not limited to such a method, and may be changed as appropriate. Blood platelets and leukocytes are contained in the buffy coat inside the BC bags 14. In the present embodiment, six BC bags 14 are provided.

A blood platelet preservation solution (PAS: Platelet Additive Solution) which serves as the medicinal solution is accommodated in the medicinal solution bag 16. As examples of the platelet additive solution, there may be cited Composol, T-sol, Intersol, Plasma LiteA, SSP, SSP+, Seto solution, M-sol, and the like.

The flow path device 10A transfers the buffy coat inside the plurality of BC bags 14 into one blood platelet bag 22 and collects the buffy coat therein, together with removing leukocytes contained within the buffy coat. Further, the flow path device 10A transfers the platelet additive solution inside the medicinal solution bag 16 into the blood platelet bag 22. A detailed configuration of the flow path device 10A will be described later.

The blood platelet bag 22 connected to the flow path device 10A is a bag for accommodating blood platelets (a blood platelet product) from which the leukocytes have been removed from the buffy coat. A non-illustrated bag for venting air is connected to the blood platelet bag 22 via a tube 28.

The flow path device 10A is equipped with a plurality of introduction tubes 30, a plurality of introduction port members 34 (first port members), a device main body 36, a single lead-out port member 38 (second port member), and a single lead-out tube 40.

In the present embodiment, seven introduction tubes 30 are provided. Ends of six introduction tubes 30 are connected respectively to the six BC bags 14, and an end of a single introduction tube 30 is connected to a sealing member 17 of the medicinal solution bag 16. It should be noted, in the description given below, the introduction tube 30 that is connected to the medicinal solution bag 16 may be referred to as an "introduction tube 30*a*".

The sealing member 17 is formed in a manner so that the interior of the medicinal solution bag 16 and the interior of the introduction tube 30*a* are placed in communication with each other by the sealing member 17 being subjected to a breaking operation. A clamp 300 for opening and closing an internal hole of the introduction tube 30*a* is provided in the introduction tube 30*a*.

Figure 2:
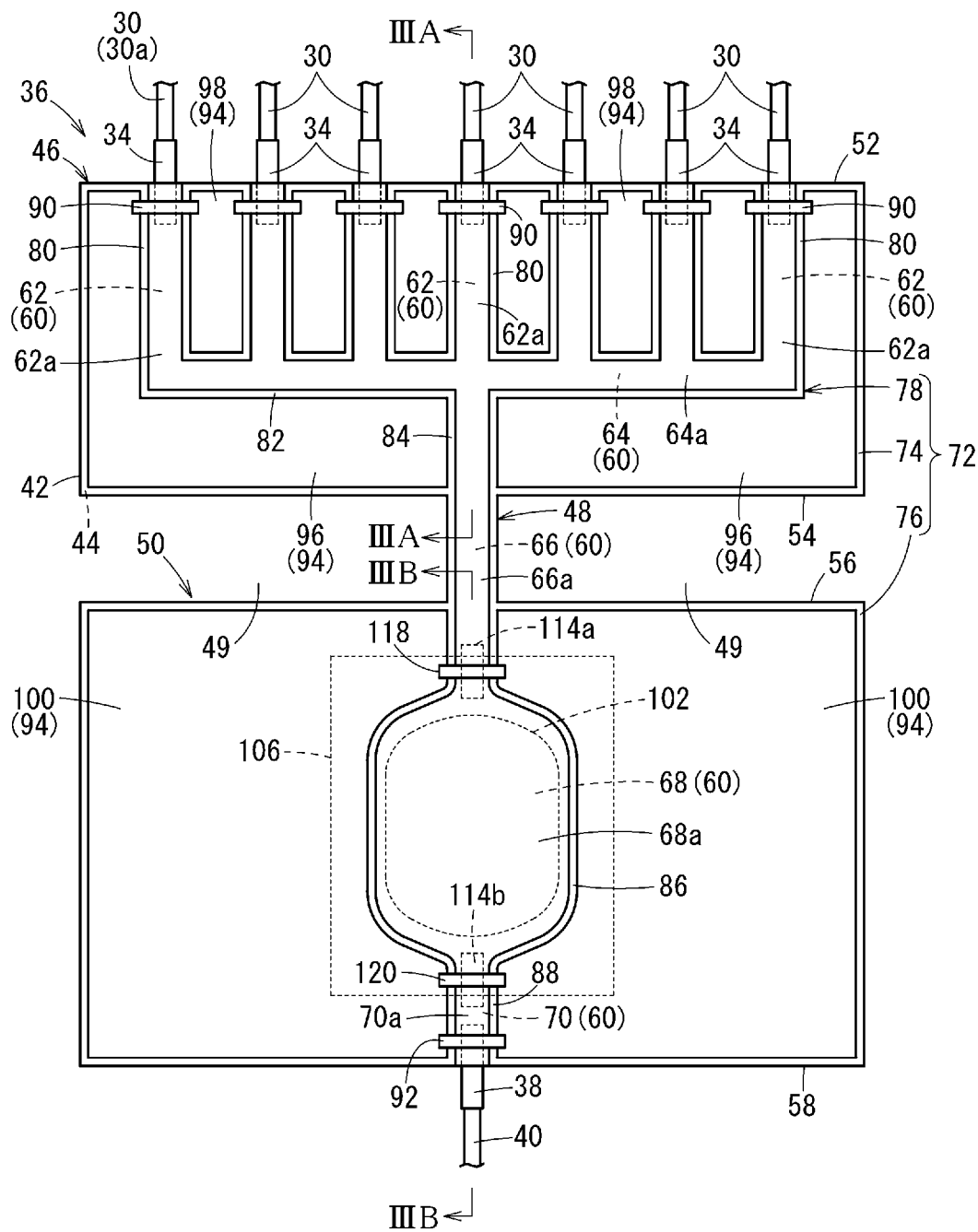
FIG. 2 is a partially enlarged plan view of the flow path device shown in FIG. 1.
Figure 3A:
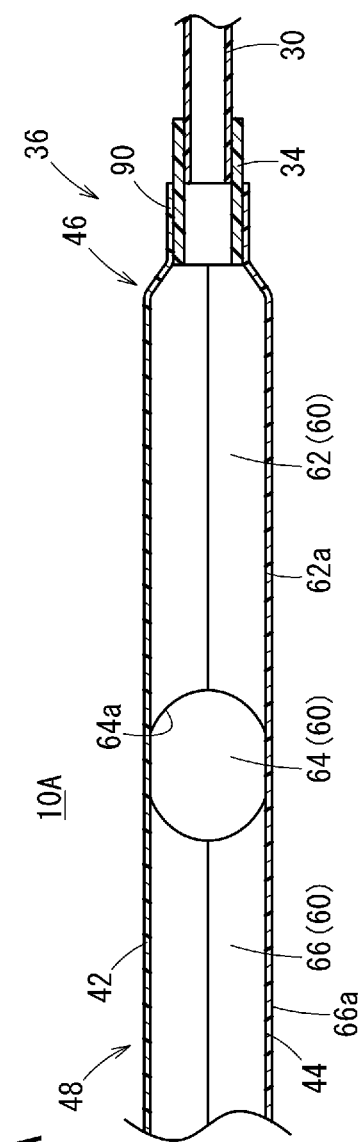
FIG. 3A is a cross-sectional view taken along line IIIA-IIIA of FIG. 2.
Figure 3B:
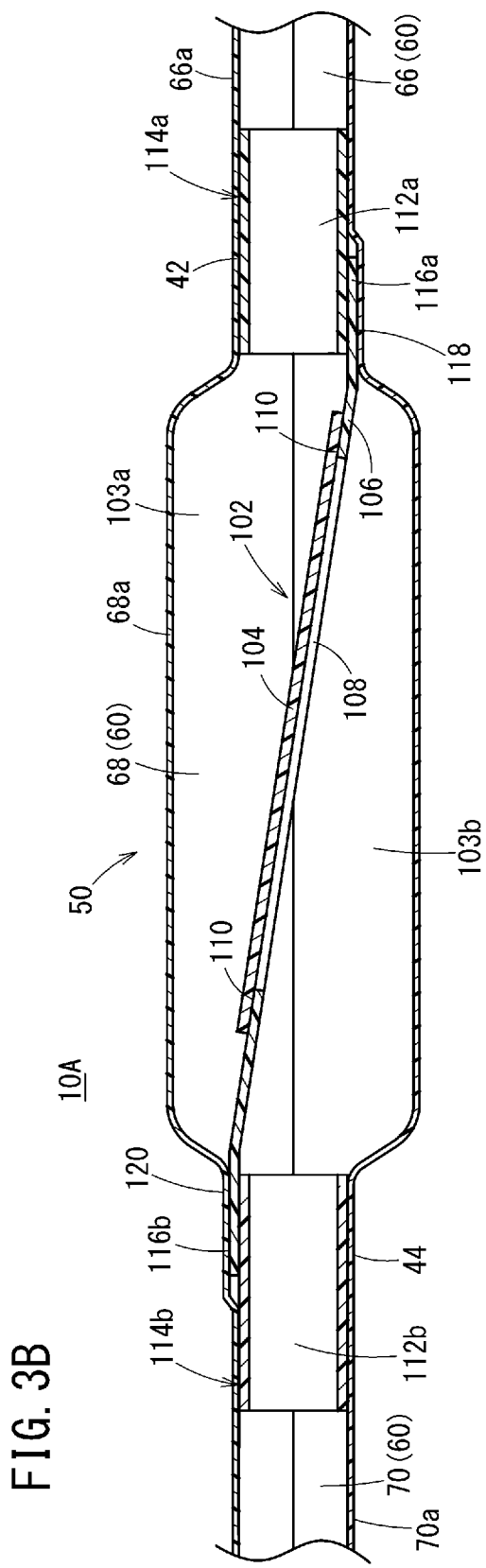
FIG. 3B is a cross-sectional view taken along line IIIB-IIIB of FIG. 2.

The device main body 36 shown in FIGS. 2 to 3B is formed in a sheet shape by a soft material. More specifically, the device main body 36 includes a first sheet 42 and a second sheet 44 formed of a soft material. As examples of such a soft material, there may be cited vinyl chloride, polyolefin, polyurethane, and the like. As examples of a vinyl chloride plasticizer, there may be cited diisononylcyclohexane-1,2-dicarboxylate, bis-2-ethylhexyl phthalate, and the like.

The first sheet 42 and the second sheet 44 are joined together mutually in a state of being superimposed in a thickness direction. As examples of the means for joining the first sheet 42 and the second sheet 44, there may be cited fusion bonding (high frequency fusion bonding, thermal fusion bonding, etc.), adhesion, and the like.

As shown in FIG. 2, the device main body 36 includes a flow path formation member 46 (first main body portion), a connecting part 48, and a filter formation member 50 (second main body portion). Each of the flow path formation member 46 and the filter formation member 50 is formed in a horizontally elongate rectangular shape. The connecting part 48 connects the flow path formation member 46 and the filter formation member 50 to each other. Spaces 49 are provided on both sides of the connecting part 48. Stated otherwise, the spaces 49 for separating the flow path formation member 46 and the filter formation member 50 from each other are provided around the periphery of the connecting part 48.

The plurality of introduction port members 34 are disposed at a first end portion 52, which is one elongate side of the flow path formation member 46. The introduction port members 34 are formed in cylindrical shapes by a hard material (for example, vinyl chloride, polyolefin, polyurethane, or the like). The plurality of introduction port members 34 are arranged at equal intervals in the longitudinal direction of the flow path formation member 46. In the present embodiment, seven of the introduction port members 34 are provided. The other ends of the introduction tubes 30 are connected respectively to the plurality of introduction port members 34. One end of the connecting part 48 is connected to a central part of a second end portion 54, which is another elongate side of the flow path formation member 46.

The other end of the connecting part 48 is connected to a central part of a third end portion 56, which is one elongate side of the filter formation member 50. One lead-out port member 38 is provided at a central part of a fourth end portion 58, which is another elongate side of the filter formation member 50. The lead-out port member 38 is configured in the same manner as the introduction port members 34. One end of the lead-out tube 40 is connected to the lead-out port member 38. The other end of the lead-out tube 40 is connected to the blood platelet bag 22 (see FIG. 1).

Liquid flow paths 60 for allowing a liquid containing at least one of the buffy coat (biological component) and a leukocyte preservation solution (medicinal solution) to flow therethrough are formed between the first sheet 42 and the second sheet 44. The liquid flow paths 60 include a plurality of first flow paths 62, an intermediate flow path 64, a second flow path 66, a filter accommodating chamber 68, and a third flow path 70.

The first flow paths 62 each extend in a straight line shape from the first end portion 52 toward the second end portion 54 of the flow path formation member 46. The plurality of first flow paths 62 are arranged alongside one another in the longitudinal direction of the flow path formation member 46 in a state of being separated from each other. The introduction port members 34 are provided in the first flow paths 62 respectively. In the present embodiment, seven of the first flow paths 62 are provided. The buffy coat is guided from the six BC bags 14 into six of the first flow paths 62. The platelet additive solution is introduced from the medicinal solution bag 16 into one of the first flow paths 62.

The intermediate flow path 64 extends along the longitudinal direction of the flow path formation member 46 (in a direction perpendicular to the direction in which the first flow paths 62 extend). The intermediate flow path 64 is connected to extending ends of the plurality of first flow paths 62. The intermediate flow path 64 enables mutual communication between the plurality of first flow paths 62 and the single second flow path 66. The intermediate flow path 64 causes the liquids introduced from the plurality of first flow paths 62 to merge together in a confluent flow.

The second flow path 66 extends in a straight line shape from the intermediate flow path 64 to the filter accommodating chamber 68. More specifically, the plurality of first flow paths 62 are located on a side opposite to the second flow path 66 (on the side of the first end portion 52) with respect to the intermediate flow path 64. The second flow path 66 communicates with a central part of the intermediate flow path 64 in the direction of extension thereof. The second flow path 66 is disposed in a straddling manner across the flow path formation member 46, the connecting part 48, and the filter formation member 50.

The filter accommodating chamber 68 is formed to be wider than the first flow paths 62, the intermediate flow path 64, the second flow path 66, and the third flow path 70. The third flow path 70 extends in a straight line shape from the filter accommodating chamber 68 to the fourth end portion 58 of the filter formation member 50. The lead-out port member 38 is provided in the third flow path 70.

The device main body 36 includes first flow path wall portions 62a, an intermediate flow path wall portion 64a, a second flow path wall portion 66a, a filter accommodating portion 68a, and a third flow path wall portion 70a. The first flow path wall portions 62a form the plurality of first flow paths 62. The intermediate flow path wall portion 64a forms the intermediate flow path 64. The second flow path wall portion 66a forms the second flow path 66.

The filter accommodating portion 68a forms the filter accommodating chamber 68. A detailed configuration of the filter accommodating portion 68a will be described later. The third flow path wall portion 70a forms the third flow path 70. The plurality of first flow path wall portions 62a, the intermediate flow path wall portion 64a, the second flow path wall portion 66a, the filter accommodating portion 68a, and the third flow path wall portion 70a bulge in convex shapes in the thickness direction of the device main body 36 in a natural state (see FIGS. 3A and 3B).

As shown in FIG. 2, sealed portions 72, which are fusion-bonded locations between the first sheet 42 and the second sheet 44, are formed in the device main body 36. The sealed portions 72 include a first outer edge sealed portion 74, a second outer edge sealed portion 76, and flow path sealed portions 78.

The first outer edge sealed portion 74 joins the first sheet 42 and the second sheet 44 to each other at an outer edge portion of the flow path formation member 46. The second outer edge sealed portion 76 joins the first sheet 42 and the second sheet 44 to each other at an outer edge portion of the filter formation member 50.

The flow path sealed portions 78 join the first sheet 42 and the second sheet 44 together in a liquid-tight manner along the liquid flow paths 60. The flow path sealed portions 78 include first flow path sealed portions 80, intermediate flow path sealed portions 82, second flow path sealed portions 84, outer peripheral sealed portions 86, and third flow path sealed portions 88.

The first flow path sealed portions 80 are provided over the entire length of the first flow paths 62 respectively on both sides of each of the plurality of the first flow paths 62. Ends of the first flow path sealed portions 80 are connected to the first outer edge sealed portion 74. The intermediate flow path sealed portions 82 are provided on both sides of the intermediate flow path 64. Other ends of the plurality of first flow path sealed portions 80 are connected to the intermediate flow path sealed portions 82.

The second flow path sealed portions 84 are provided over the entire length of the second flow path 66 on both sides of the second flow path 66. One end of each of the second flow path sealed portions 84 is connected to the intermediate flow path sealed portions 82. The first outer edge sealed portion 74 and the second outer edge sealed portion 76 are connected to an intermediate portion of the second flow path sealed portions 84. One end of each of the second flow path sealed portions 84 and one end of the second flow path wall portion 66a form one part of the flow path formation member 46. Another end of each of the second flow path sealed portions 84 and another end of the second flow path wall portion 66a form one part of the filter formation member 50. An intermediate portion of each of the second flow path sealed portions 84 and an intermediate portion of the second flow path wall portion 66a form the connecting part 48. Spaces 49 are provided on both sides of the intermediate portion of the second flow path sealed portions 84. A clamp 302 for opening and closing the second flow path 66 is provided at the intermediate portion of the second flow path wall portion 66a.

The outer peripheral sealed portions 86 are provided so as to surround the filter accommodating portion 68a. Another end of each of the second flow path sealed portions 84 is connected to the corresponding one of the outer peripheral sealed portions 86. The third flow path sealed portions 88 are provided over the entire length of the third flow path 70 on both sides of the third flow path 70. One end of each of the third flow path sealed portions 88 is connected to the corresponding one of the outer peripheral sealed portions 86. Another end of each of the third flow path sealed portions 88 is connected to the second outer edge sealed portion 76.

A plurality of introduction side fixing members 90 and a lead-out side fixing member 92 are provided in the device main body 36. The introduction side fixing members 90 fix the introduction port members 34 to the flow path formation member 46. The introduction side fixing members 90 extend in a direction perpendicular to (intersecting with) the direction of extension of the introduction port members 34. The first sheet 42 and the second sheet 44 are fixed to each other at both ends of the introduction side fixing members 90. In central parts of the introduction side fixing members 90, the first sheet 42 and the introduction port members 34 are fixed (sealed) to each other, and the second sheet 44 and the introduction port members 34 are fixed (sealed) to each other (see FIG. 3A).

The lead-out side fixing member 92 fixes the lead-out port member 38 to the filter formation member 50. The lead-out side fixing member 92 extends in a direction perpendicular to (intersecting with) the direction of extension of the lead-out port member 38. The first sheet 42 and the second sheet 44 are fixed to each other at both ends of the lead-out side fixing member 92. In a central part of the lead-out side fixing member 92, the first sheet 42 and the lead-out port member 38 are fixed (sealed) to each other, and the second sheet 44 and the lead-out port member 38 are fixed (sealed) to each other (see FIG. 3B).

Non-sealed portions 94 where the first sheet 42 and the second sheet 44 are not joined (fusion bonded) to each other are provided at portions other than the liquid flow paths 60 within the device main body 36. The non-sealed portions 94 do not bulge outwardly in the thickness direction. The non-sealed portions 94 are formed to be thicker than the sealed portions 72. The non-sealed portions 94 are disposed along the flow path sealed portions 78.

The non-sealed portions 94 include first non-sealed portions 96, second non-sealed portions 98, and third non-sealed portions 100. The first non-sealed portions 96 are surrounded by the most outwardly positioned first flow path sealed portions 80, the intermediate flow path sealed portions 82, one end of each of the second flow path sealed portions 84, and the first outer edge sealed portion 74. The second non-sealed portions 98 are positioned between the first flow path sealed portions 80 that lie adjacent to each other. More specifically, the first outer edge sealed portion 74 extends so as to surround the first non-sealed portions 96 and the second non-sealed portions 98.

The third non-sealed portions 100 are surrounded by the other end of each of the second flow path sealed portions 84, the outer peripheral sealed portions 86, the third flow path sealed portions 88, and the second outer edge sealed portion 76. More specifically, the second outer edge sealed portion 76 extends so as to surround the third non-sealed portions 100.

The filter accommodating portion 68a is positioned substantially in the center of the filter formation member 50, and accommodates a filter member 102. As shown in FIG. 3B, the filter accommodating chamber 68 is partitioned by the filter member 102 into a first chamber 103a and a second chamber 103b in the thickness direction of the filter formation member 50.

The filter member 102 includes a filter main body 104 and a support sheet 106 that supports the filter main body 104. The filter main body 104 is a filter medium that separates (removes or traps) leukocytes (a predetermined biological component) from the buffy coat (biological fluid). The filter main body 104 is made of a sheet-shaped porous body having fine communication holes that communicate from one surface to the other surface thereof. As examples of such a porous body, there may be cited polyurethane sponge sheets and non-woven fabrics. Although detailed illustration thereof is omitted, the filter main body 104 is formed by laminating a plurality of sheets (for example, on the order of two to ten sheets). However, in the filter main body 104, a single sheet may be provided.

The support sheet 106 is formed by a resin material in a manner so that liquid is incapable of passing therethrough. As shown in FIG. 2, the outer shape of the support sheet 106 is formed in a rectangular shape. The longitudinal direction of the support sheet 106 lies along the lateral direction (short-side direction) of the filter formation member 50. The support sheet 106 extends peripherally around the outer side of the filter main body 104.

As shown in FIG. 3B, a hole 108 which is covered by the filter main body 104 is formed in a central part of the support sheet 106. The hole 108 extends in the direction in which the support sheet 106 extends. A filter sealed portion 110 is provided on an outer peripheral side of the hole 108 of the support sheet 106 in order to prevent the liquid (biological component) from flowing between the filter main body 104 and the support sheet 106. The filter sealed portion 110 joins the filter main body 104 to the support sheet 106 in a liquid-tight manner. The filter sealed portion 110 extends once around the outer peripheral edge of the filter main body 104. The outer peripheral edge of the support sheet 106 is joined (fusion bonded) to the first sheet 42 and the second sheet 44 by the outer peripheral sealed portions 86 (see FIG. 2).

As shown in FIGS. 2 and 3B, a first tube 114a having an inner hole 112a in communication with the first chamber 103a is disposed in an end of the second flow path 66 on the side of the filter accommodating chamber 68. The first tube 114a extends along the lateral direction of the filter formation member 50. A first portion 116a of the support sheet 106 is sandwiched between the first tube 114a and the second sheet 44.

The first tube 114a and the first portion 116a of the support sheet 106 are fixed to the filter formation member 50 by a first fixing member 118. The first fixing member 118 extends along the longitudinal direction of the filter formation member 50 in a manner so as to intersect the first tube 114a. The first sheet 42 and the second sheet 44 are fixed (sealed) to each other at both ends of the first fixing member 118. At a central part of the first fixing member 118, the second sheet 44 and the first portion 116a of the support sheet 106 are fixed (sealed) to each other, the first portion 116a of the support sheet 106 and the first tube 114a are fixed (sealed) to each other, and the first sheet 42 and the first tube 114a are fixed (sealed) to each other.

A second tube 114b having an inner hole 112b in communication with the second chamber 103b is disposed in an end of the third flow path 70 on the side of the filter accommodating chamber 68. The first tube 114a and the second tube 114b are disposed so as to face each other with the filter accommodating chamber 68 interposed therebetween. The second tube 114b extends along the lateral direction of the filter formation member 50. A second portion 116b of the support sheet 106 is sandwiched between the second tube 114b and the first sheet 42.

The second tube 114b and the second portion 116b of the support sheet 106 are fixed to the filter formation member 50 by a second fixing member 120. The second fixing member 120 extends along the longitudinal direction of the filter formation member 50 in a manner so as to intersect the second tube 114b. The first sheet 42 and the second sheet 44 are fixed (sealed) to each other at both ends of the second fixing member 120. At a central part of the second fixing member 120, the first sheet 42 and the second portion 116b of the support sheet 106 are fixed (sealed) to each other, the second portion 116b of the support sheet 106 and the second tube 114b are fixed (sealed) to each other, and the second sheet 44 and the second tube 114b are fixed (sealed) to each other.

Figure 4B:
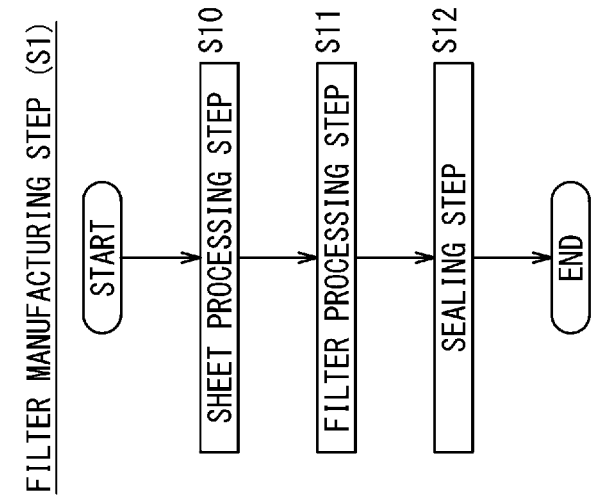
FIG. 4B is a flowchart provided to explain a method of manufacturing a filter shown in FIG. 4A.
Figure 4A:
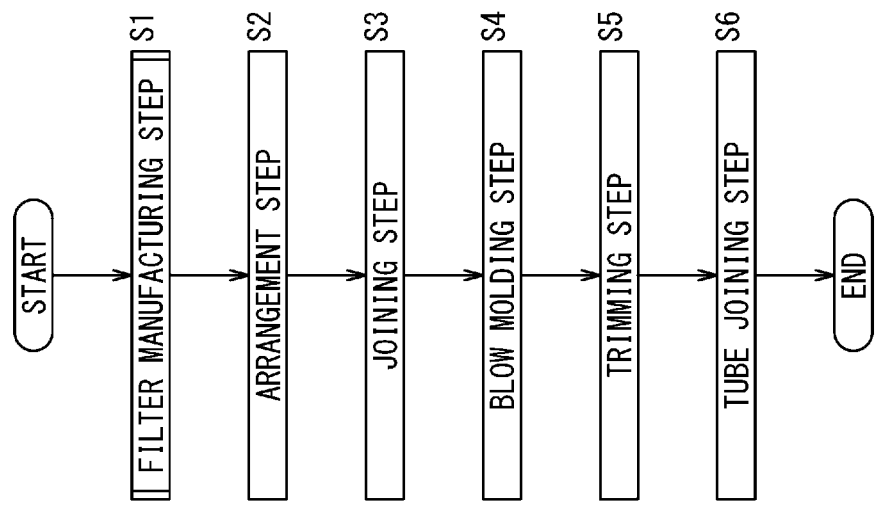
FIG. 4A is a flowchart provided to explain a method of manufacturing the flow path device shown in FIG. 2.

As shown in FIG. 4A, the method of manufacturing the flow path device 10A provided with the above-described configuration includes a filter manufacturing step, an arrangement step, a joining step, a blow molding step, a trimming step, and a tube joining step.

Figure 5A:
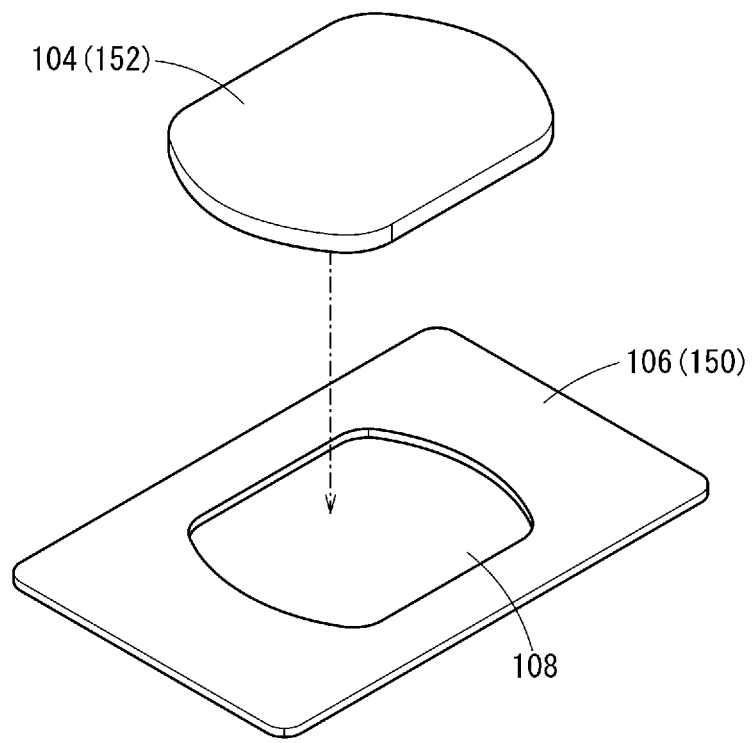
FIG. 5A is an explanatory diagram of a sheet processing step and a filter processing step of FIG. 4B.

As shown in FIG. 4B, the filter manufacturing step (step S1 in FIG. 4A) includes a sheet processing step, a filter processing step, and a sealing step. In the sheet processing step (step S10 in FIG. 4B), as shown in FIG. 5A, a sheet material 150 is punched out into a rectangular shape, and the hole 108 is punched out in a central part of the rectangular shape to thereby form the support sheet 106. Moreover, in the sheet processing step, the sheet material 150 may be cut out into the shape of the support sheet 106 using a laser machining device or the like. In the filter processing step (step S11), the filter main body 104 is formed by punching out a filter material 152 of a sheet shape. The filter main body 104 is formed to be slightly larger than the hole 108 of the support sheet 106.

Figure 5B:
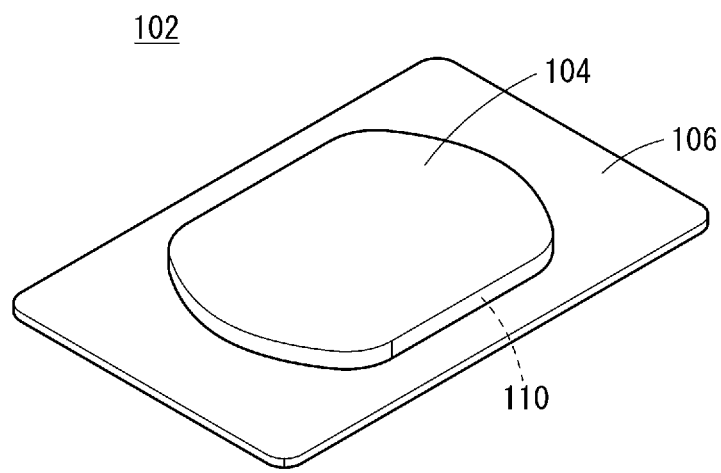
FIG. 5B is an explanatory diagram of a sealing step shown in FIG. 4B.

Subsequently, in the sealing step (step S12), as shown in FIG. 5B, the outer peripheral edge of the filter main body 104 is circumferentially joined to the support sheet 106 in a state of the filter main body 104 being superimposed on one surface of the support sheet 106 so as to cover the hole 108 of the support sheet 106, thereby forming the filter sealed portion 110. Consequently, the filter member 102 is manufactured.

Figure 6:
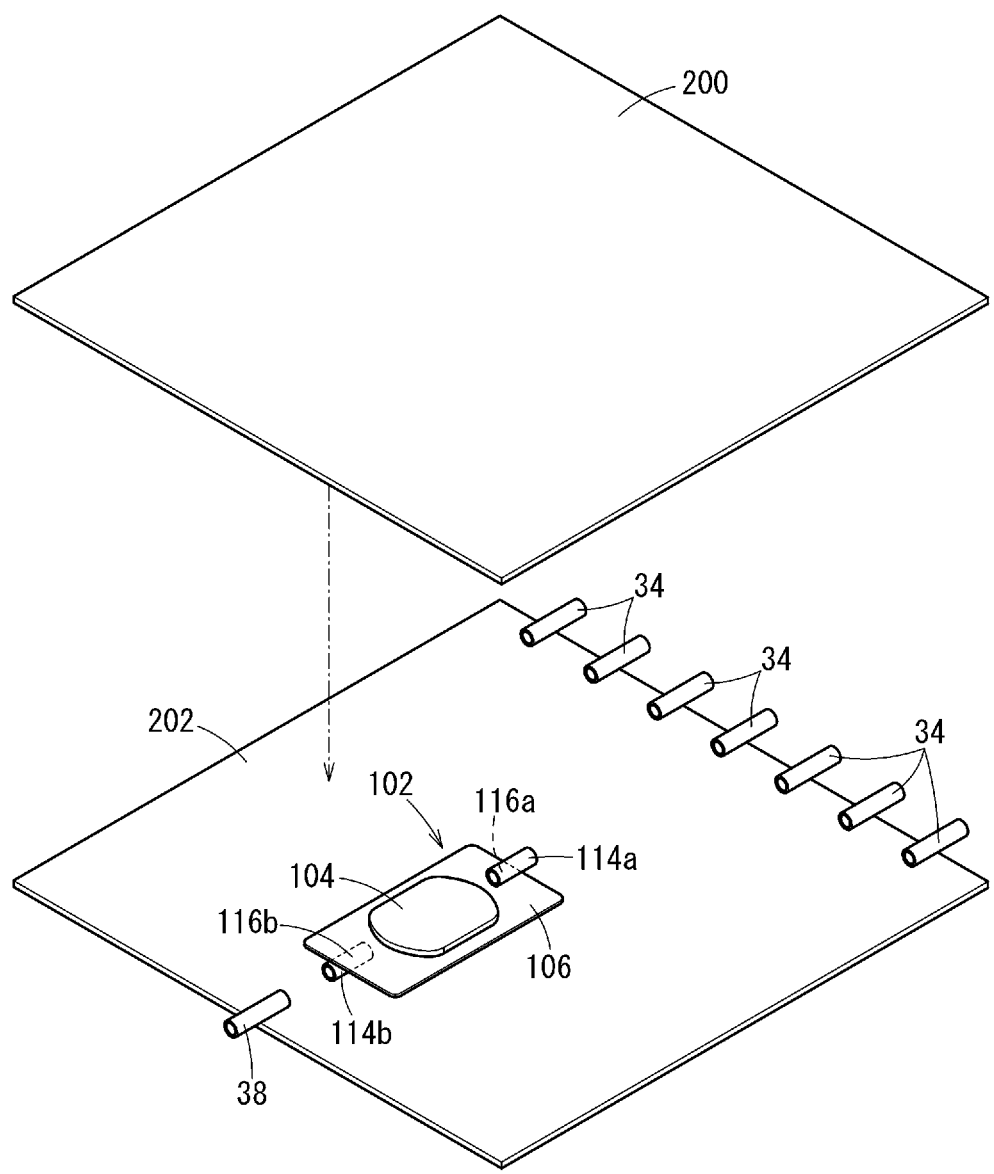
FIG. 6 is an explanatory diagram of an arrangement step shown in FIG. 4A.

Next, in the arrangement step (step S2 of FIG. 4A), as shown in FIG. 6, the plurality of (seven) introduction port members 34, one lead-out port member 38, the filter member 102, the first tube 114a, and the second tube 114b are set so as to be arranged between a rectangular first material sheet 200 that is formed by a soft material, and a rectangular second material sheet 202 that is formed by a soft material.

The plurality of introduction port members 34 are arranged between one end of the first material sheet 200 and one end of the second material sheet 202. The lead-out port member 38 is arranged between another end of the first material sheet 200 and another end of the second material sheet 202. The filter member 102 is arranged between a central part of the first material sheet 200 and a central part of the second material sheet 202. The first portion 116a of the support sheet 106 is disposed between the first tube 114a and the second material sheet 202, and the second portion 116b of the support sheet 106 is disposed between the second tube 114b and the first material sheet 200.

In addition, in the joining step (step S3 of FIG. 4A), the plurality of introduction port members 34 are joined to the first material sheet 200 and the second material sheet 202, together with the lead-out port member 38 being joined to the first material sheet 200 and the second material sheet 202. Further, as shown in FIG. 7A, the first portion 116a is joined to the second material sheet 202 and the first tube 114a, together with the second portion 116b being joined to the first material sheet 200 and the second tube 114b. In this case, during such joining, a high-frequency fusion bonding device, or a heat fusion bonding device or the like is used.

A first intermediate product 204 obtained in the joining step is placed at a predetermined position between a pair of molds 208a and 208b that constitute a sheet joining device 206 shown in FIG. 7B. In the present embodiment, the sheet joining device 206 is a high frequency (radio frequency) fusion bonding device. The sheet joining device 206 may also be a heat fusion bonding device or the like. Grooves for forming portions (convex wall portions) that surround the liquid flow paths 60 of the device main body 36 are provided on the molding surfaces of the pair of molds 208a and 208b.

Thereafter, in the blow molding step (step S4 of FIG. 4A), as shown in FIG. 7B, the first material sheet 200 and the second material sheet 202 are sandwiched between the molds 208a and 208b, and the first material sheet 200 and the second material sheet 202 are joined to each other, together with blow molding being performed so as to form the liquid flow paths 60 in which the filter member 102 is arranged.

More specifically, the pair of molds 208a and 208b are closed, the first material sheet 200 and the second material sheet 202 are overlapped, and predetermined locations of the first material sheet 200 and the second material sheet 202 are subjected to high frequency fusion bonding so as to form the liquid flow paths 60 (the plurality of first flow paths 62, the intermediate flow path 64, the second flow path 66, the filter accommodating chamber 68, and the third flow path 70). At this time, air is blown out from a non-illustrated blow nozzle, and in the first material sheet 200 and the second material sheet 202, locations thereof corresponding to the grooves provided in the molds 208a and 208b are inflated, whereby the liquid flow paths 60 are formed.

After completion of the blow molding step, the blow nozzle is pulled out from the device main body 36. Next, the pair of molds 208a and 208b are opened, and a second intermediate product 210 is taken out.

Subsequently, in the trimming step (step S5 of FIG. 4A), as shown in FIG. 8, both sides of the second flow path 66 of the second intermediate product 210 are cut along a cutting line CT and removed. Consequently, the connecting part 48 that connects the flow path formation member 46 and the filter formation member 50 to each other is formed. Stated otherwise, the flow path device 10A is formed. In particular, the spaces 49 are formed on both sides of the connecting part 48.

Thereafter, in the tube joining step (step S6 of FIG. 4A), the introduction tubes 30 are joined respectively to the plurality of introduction port members 34, and the lead-out tube 40 is joined to the lead-out port member 38. Consequently, by carrying out the aforementioned steps, the flow path device 10A is manufactured.

Figure 9:
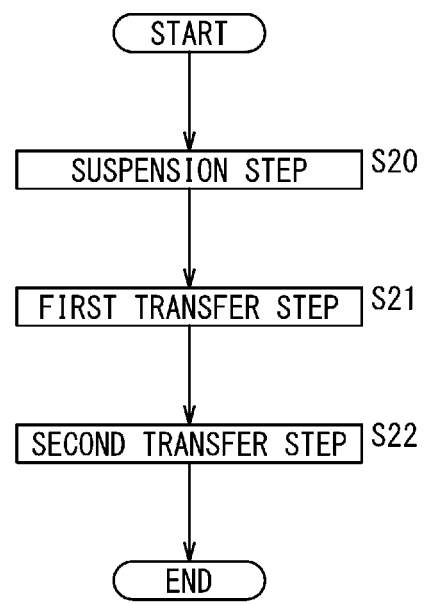
FIG. 9 is a flowchart for describing a blood platelet collection method in which the biological component bag system shown in FIG. 1 is used.

Next, a blood platelet collection method for obtaining blood platelets from which leukocytes have been removed from the buffy coat using the biological component bag system 12 will be described. Moreover, the buffy coat inside each of the BC bags 14 contains leukocytes and blood platelets, whereas the content ratio of concentrated red blood cells and plasma contained therein is relatively small. As shown in FIG. 9, the blood platelet collection method includes a suspension step, a first transfer step, and a second transfer step.

Figure 10:
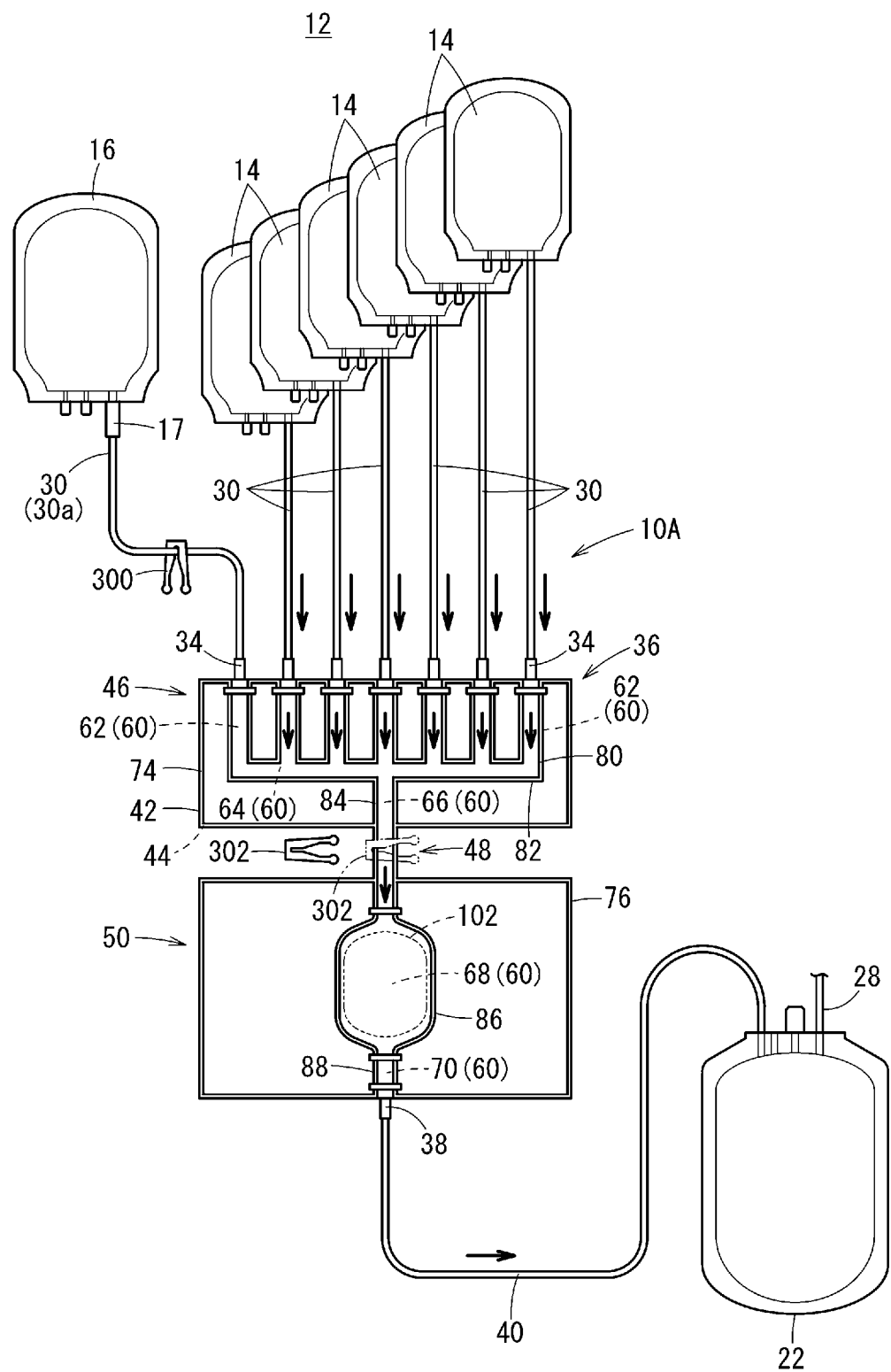
FIG. 10 is an explanatory diagram of a suspension step and a first transfer step shown in FIG. 9.

As shown in FIG. 10, at first, in the suspension step (step S20 of FIG. 9), the plurality of BC bags 14 and the medicinal solution bag 16 are suspended on a non-illustrated suspension platform. At this time, the flow path device 10A is suspended by the introduction tubes 30. In greater detail, the blood platelet bag 22 is located at a more downward (vertically downward) position than the plurality of BC bags 14 and the medicinal solution bag 16.

Next, in the first transfer step (step S21 of FIG. 9), the clamp 302 is opened. Upon doing so, due to the action of gravity (difference in elevation), the buffy coat inside the plurality of BC bags 14 is transferred into the first chamber 103a of the filter accommodating portion 68a via the plurality of introduction tubes 30, the plurality of first flow paths 62, the intermediate flow path 64, and the second flow path 66. At this time, the filter formation member 50 may be temporarily inverted vertically in position in order to discharge the air inside the filter accommodating chamber 68 to the exterior. Consequently, since the air inside the filter accommodating chamber 68 is efficiently discharged to the exterior, the area through which the buffy coat flows with respect to the filter main body 104 can be effectively increased. Moreover, after the air inside the filter accommodating chamber 68 is discharged, the filter formation member 50 is returned to its original state.

The buffy coat that has flowed into the first chamber 103a passes through the filter main body 104 and flows into the second chamber 103b. At this time, the leukocytes are removed from the buffy coat. The blood platelets, which are obtained by removing the leukocytes from the buffy coat, are guided into the blood platelet bag 22 from the second chamber 103b via the third flow path 70 and the lead-out tube 40.

Upon completion of the first transfer step, then in the second transfer step (step S22 of FIG. 9), the sealing member 17 of the medicinal solution bag 16 is broken together with opening the clamp 300. Upon doing so, due to the action of gravity (difference in elevation), the platelet additive solution in the medicinal solution bag 16 is introduced into the blood platelet bag 22 via the introduction tube 30a, the first flow paths 62, the intermediate flow path 64, the second flow path 66, the filter accommodating chamber 68, the third flow path 70, and the lead-out tube 40. Consequently, it is possible to obtain blood platelets (a blood platelet product) in which leukocytes are not included.

In this case, the flow path device 10A and the biological component bag system 12 according to the present embodiment exhibit the following advantageous effects.

In the flow path device 10A, the liquid flow paths 60 include the plurality of first flow paths 62, the single second flow path 66, the intermediate flow path 64, the filter accommodating chamber 68 in which the filter member 102 is accommodated, and the third flow path 70. The device main body 36 includes the first sheet 42 that is formed by a soft material, and the second sheet 44 that is formed by a soft material and is superimposed on the first sheet 42. The liquid flow paths 60 are formed between the first sheet 42 and the second sheet 44. In the device main body 36, the flow path sealed portions 78 that join the first sheet 42 and the second sheet 44 to each other in a liquid-tight manner are disposed along the liquid flow paths 60.

In accordance with such a configuration, the liquid flow paths 60 (the plurality of first flow paths 62, the intermediate flow path 64, the second flow path 66, and the filter accommodating chamber 68) are formed between the first sheet 42 and the second sheet 44. Therefore, compared to a conventional product in which a plurality of branch connectors and a plurality of tubes are used, the number of component parts of the flow path device 10A can be reduced. Further, the flow path sealed portions 78 are provided along the liquid flow paths 60. Consequently, in the flow path device 10A, since there is no need to join a large number of component parts, the number of joining steps can be reduced. Thus, a reduction in costs can be achieved.

The flow path sealed portions 78 include the first flow path sealed portions 80 provided respectively on both sides of each of the plurality of first flow paths 62, the intermediate flow path sealed portions 82 provided on both sides of the intermediate flow path 64, the second flow path sealed portions 84 provided on both sides of the second flow path 66, the outer peripheral sealed portions 86 provided along the outer periphery of the filter accommodating chamber 68, and the third flow path sealed portions 88 provided on both sides of the third flow path 70.

In accordance with such a configuration, leakage of liquid from the first flow paths 62, the intermediate flow path 64, the second flow path 66, the filter accommodating chamber 68, and the third flow path 70 can be effectively suppressed.

The spaces 49 are provided on both sides of the second flow path sealed portions 84.

In accordance with such a configuration, the clamp 302 for opening and closing the second flow path 66 can be easily attached to and detached from the second flow path wall portion 66a that forms the second flow path 66.

The non-sealed portions 94 where the first sheet 42 and the second sheet 44 are not joined to each other are provided at portions other than the liquid flow paths 60 within the device main body 36. The non-sealed portions 94 are disposed along the first flow path sealed portions 80, the intermediate flow path sealed portions 82, the second flow path sealed portions 84, the outer peripheral sealed portions 86, and the third flow path sealed portions 88.

In accordance with such a configuration, the first flow path sealed portions 80, the intermediate flow path sealed portions 82, the second flow path sealed portions 84, the outer peripheral sealed portions 86, and the third flow path sealed portions 88 can be protected by the non-sealed portions 94.

The first outer edge sealed portion 74 and the second outer edge sealed portion 76, which extend in a manner so as to surround the non-sealed portions 94 and join the first sheet 42 and the second sheet 44 to each other, are provided in the device main body 36.

In accordance with such a configuration, the non-sealed portions 94 can be protected by the first outer edge sealed portion 74 and the second outer edge sealed portion 76.

(First Modification)

Next, a flow path device 10B according to a first modification will be described. In the flow path device 10B according to the present modification, constituent elements thereof, which are the same as those of the above-described flow path device 10A, are designated with the same reference characters, and detailed description of such features is omitted. The same convention applies to a flow path device 10C according to a second modification and a flow path device 10D according to a third modification, which will be described later.

As shown in FIG. 11, in the liquid flow paths 60a of the device main body 36a (the flow path formation member 46a) of the flow path device 10B, a plurality of (seven) introduction flow paths 220 are included that communicate respectively with the plurality of (seven) first flow paths 62. The device main body 36a includes a plurality of introduction flow path wall portions 220a that form the plurality of introduction flow paths 220. The flow path sealed portions 78a of the sealed portions 72a include introduction flow path sealed portions 222 provided respectively on both sides of each of the plurality of introduction flow paths 220.

The introduction flow path sealed portions 222 extend along the outer shape of the device main body 36a. More specifically, the non-sealed portions 94 do not exist on both sides of the introduction flow path sealed portions 222. Therefore, spaces 223 that extend along the introduction flow path sealed portions 222 are formed between the introduction flow path sealed portions 222 that lie adjacent to each other.

In the flow path device 10B, the introduction port members 34 described above are omitted. Further, instead of the aforementioned six introduction tubes 30, six introduction flow path wall portions 220a are provided and thus are connected respectively to the six BC bags 14. Instead of the aforementioned single introduction tube 30a, one of the introduction flow path wall portions 220a is provided and thus is connected to the sealing member 17 of the medicinal solution bag 16. The clamp 300 (see FIG. 1) is provided on the introduction flow path wall portion 220a that is connected to the medicinal solution bag 16.

In the flow path device 10B according to the present modification, the same effects are exhibited as those of the above-described flow path device 10A. In the present modification, the liquid flow paths 60a include the plurality of introduction flow paths 220 that communicate respectively with the plurality of first flow paths 62. The flow path sealed portions 78a include the introduction flow path sealed portions 222 provided respectively on both sides of each of the plurality of introduction flow paths 220. The spaces 223 that extend along the introduction flow path sealed portions 222 are formed between the introduction flow path sealed portions 222 that lie adjacent to each other.

In accordance with such a configuration, since the plurality of introduction flow paths 220 can be integrally provided in the device main body 36a, the cost of the flow path device 10B can be further reduced. Further, since the spaces 223 are formed between the introduction flow path sealed portions 222 that lie adjacent to each other, the plurality of introduction flow paths 220 can be freely arranged without interfering with each other. Furthermore, the clamp 300 can be easily attached to and detached from the introduction flow path wall portion 220a that forms the introduction flow path 220.

(Second Modification)

Next, a flow path device 10C according to a second modification will be described. As shown in FIG. 12, in the device main body 36b (the flow path formation member 46b) of the flow path device 10C according to the present modification, trimming (cutting) is carried out on the aforementioned first non-sealed portions 96 and the second non-sealed portions 98. In other words, the sealed portions 72b of the device main body 36b do not include the aforementioned first outer edge sealed portion 74. The first flow path sealed portions 80, the intermediate flow path sealed portions 82, and the second flow path sealed portions 84 extend along the outer shape of the device main body 36b.

In the flow path device 10C according to the present modification, the same effects are exhibited as those of the above-described flow path device 10A. In the present modification, the first flow path sealed portions 80, the intermediate flow path sealed portions 82, and the second flow path sealed portions 84 extend along the outer shape of the device main body 36b.

In accordance with such a configuration, the device main body 36b can be made smaller in size.

In the present modification, as in the flow path device 10B according to the first modification, the introduction flow path wall portions 220a may be provided instead of the plurality of introduction tubes 30.

(Third Modification)

Next, a flow path device 10D according to a third modification will be described. As shown in FIG. 13, the liquid flow paths 60b of the device main body 36c of the flow path device 10D according to the present modification include a plurality of (four) first flow paths 62, and a second flow path 66 that communicates directly with the plurality of first flow paths 62. Stated otherwise, the liquid flow paths 60b do not include the above-described intermediate flow path 64. The plurality of first flow path wall portions 62a are directly connected to the second flow path wall portion 66a.

The sealed portions 72c include the first outer edge sealed portion 74 and the flow path sealed portions 78b. The flow path sealed portions 78b include the first flow path sealed portions 80, and the second flow path sealed portions 84 that are directly connected to the first flow path sealed portions 80.

In the flow path device 10D according to the present modification, the same effects are exhibited as those of the above-described flow path device 10A.

In the present modification, as in the flow path device 10B according to the first modification, the introduction flow paths 220 may be provided instead of the plurality of introduction tubes 30.

The present invention is not limited to the above-described embodiment, and various modifications may be adopted within a range that does not depart from the essence and gist of the present invention.

The configurations of the flow paths formed in the device main bodies 36 and 36a to 36c, and the number and arrangement of the bags (the BC bags 14 and the medicinal solution bag 16) that are provided are not limited to the configurations described and illustrated above, and modifications may be made thereto in accordance with the type of biological component and the method of use. Further, the number of introduction tubes 30, the number of introduction flow paths 220, and the number of first flow paths 62 are not limited to seven or four, and can be appropriately changed to any number that is greater than or equal to two.

In the biological component bag system 12, sealing members, which block communication between the interiors of the BC bags 14 and the interiors of the introduction tubes 30 in an initial state, may be provided in the respective BC bags 14. The sealing members are formed in a manner so that the interiors of the BC bags 14 and the interiors of the introduction tubes 30 are placed in communication with each other by being subjected to a breaking operation. The introduction tubes 30 may be directly fusion bonded to the device main bodies 36, 36b and 36c without using the introduction port members 34. The lead-out tube 40 may be directly fusion bonded to the device main bodies 36 and 36a to 36c without using the lead-out port member 38.

The above-described embodiment can be summarized in the following manner.

In the above-described embodiment, the flow path device (10A to 10D) is disclosed in which there are formed the flow paths (60, 60a) that allow at least one liquid of the biological fluid and the medicinal solution to flow therethrough, the flow path device including the device main body (36, 36a to 36c) in which the flow paths are formed, the device main body including the first sheet (42) formed by a soft material, and the second sheet (44) formed by a soft material and that is superimposed on the first sheet, wherein the flow paths are formed between the first sheet and the second sheet, the flow paths including the plurality of first flow paths (62), and the single second flow path (66) that communicates with the plurality of first flow paths, the filter accommodating chamber (68) provided in the second flow path and in which there is accommodated the filter member (102) for removing a predetermined biological component in the biological fluid, and the third flow path (70) through which the liquid having passed through the filter accommodating chamber flows, wherein flow path sealed portions (78, 78a, 78b), which join the first sheet and the second sheet to each other in a liquid-tight manner, are provided in the device main body.

In the above-described flow path device, the flow paths may include the intermediate flow path (64) that places the plurality of first flow paths and the second flow path in communication with each other.

In the above-described flow path device, the flow path sealed portions may include the first flow path sealed portions (80) provided on both sides of each of the plurality of first flow paths, the intermediate flow path sealed portions (82) provided on both sides of the intermediate flow path, the second flow path sealed portions (84) provided on both sides of the second flow path, the outer peripheral sealed portions (86) provided along the outer periphery of the filter accommodating chamber, and the third flow path sealed portions (88) provided on both sides of the third flow path.

In the above-described flow path device, the spaces (49) may be provided on both sides of the second flow path sealed portions.

In the above-described flow path device, the non-sealed portions (94) where the first sheet and the second sheet are not joined to each other may be provided at positions other than the flow paths within the device main body, and the non-sealed portions may be disposed along the first flow path sealed portions, the intermediate flow path sealed portions, the second flow path sealed portions, the outer peripheral sealed portions, and the third flow path sealed portions.

In the above-described flow path device, the outer edge sealed portions (74 and 76), which extend in a manner so as to surround the non-sealed portions and join the first sheet and the second sheet to each other, may be provided in the device main body.

In the above-described flow path device, in the flow path sealed portions, there may be provided the plurality of first port members (34) that form ports in communication respectively with the plurality of first flow paths, and a single second port member (38) that forms a port in communication with the third flow path.

In the above-described embodiment, the flow path device is disclosed in which there are formed the flow paths that allow at least one liquid of the biological fluid and the medicinal solution to flow therethrough, the flow path device including the device main body in which there are provided the sealed portions that mutually join the plurality of sheets formed by a soft material in a liquid-tight manner to thereby form the flow paths in the interior of the sheets, wherein the device main body is made up from the first main body portion (46), the second main body portion (50), and the connecting part (48) connecting the first main body portion and the second main body portion, the first main body portion including the plurality of first flow paths, and the second flow path in communication with the plurality of first flow paths, the second main body portion including the filter accommodating chamber provided in the second flow path and in which there is accommodated the filter member that removes a predetermined biological component in the biological fluid, and the third flow path through which the liquid having passed through the filter accommodating chamber flows, wherein the connecting part forms at least a portion of the second flow path.

In the above-described embodiment, the spaces for separating the first main body portion and the second main body portion from each other may be provided around the periphery of the connecting part.

In the above-described embodiment, the biological component bag system (12) is disclosed which collects a desired biological component from the biological fluid, the biological component bag system including the plurality of first bags (14) in which the biological fluid is accommodated, the flow path device to which the plurality of first bags are connected, and the second bag (22) for accommodating the biological component which is guided from the plurality of first bags via the flow path device, wherein the flow path device is the flow path device described above.

In the above-described biological component bag system, there may further be provided the medicinal solution bag (16) connected to the flow path device, and in which there is accommodated the medicinal solution to be added to the second bag via the flow path device.

In the above-described biological component bag system, the buffy coat as the biological fluid may be accommodated in each of the plurality of first bags, the platelet additive solution as the medicinal solution may be accommodated in the medicinal solution bag, the filter member of the flow path device may remove leukocytes from the buffy coat, and the blood platelets that have passed through the flow path device, and the platelet additive solution may be accommodated in the second bag.

What is claimed is:
1. A flow path device in which there are formed flow paths configured to allow at least one liquid of a biological fluid and a medicinal solution to flow therethrough, the flow path device comprising:
a device main body comprising:
a first sheet formed by a soft material; and a second sheet formed by a soft material and that is superimposed on the first sheet, wherein the device main body comprises a first portion including:
a plurality of first flow paths;
a plurality of first ports at a first edge of the first portion and in communication with the plurality of first flow paths;
a single second flow path configured to communicate with the plurality of first flow paths; and
a second port in communication with the single second flow path and at a second edge of the first portion opposite the first edge;
a filter accommodating chamber provided in the single second flow path and in which there is accommodated a filter member configured to remove a predetermined biological component in the biological fluid; and
a third flow path through which the liquid having passed through the filter accommodating chamber flows;
wherein flow path sealed portions, which are configured to join the first sheet and the second sheet to each other in a liquid-tight manner, are provided in the device main body.

2. The flow path device according to claim 1, wherein an intermediate flow path is configured to place the plurality of first flow paths and the single second flow path in communication with each other.

3. The flow path device according to claim 2, wherein the flow path sealed portions comprise:
first flow path sealed portions provided on both sides of each of the plurality of first flow paths;
intermediate flow path sealed portions provided on both sides of the intermediate flow path;
second flow path sealed portions provided on both sides of the single second flow path;
outer peripheral sealed portions provided along an outer periphery of the filter accommodating chamber; and
third flow path sealed portions provided on both sides of the third flow path.

4. The flow path device according to claim 3, wherein spaces are provided on both sides of the second flow path sealed portions.

5. The flow path device according to claim 3, wherein:
non-sealed portions where the first sheet and the second sheet are not joined to each other are provided at positions other than the flow paths within the device main body; and
the non-sealed portions are disposed along the first flow path sealed portions, the intermediate flow path sealed portions, the second flow path sealed portions, the outer peripheral sealed portions, and the third flow path sealed portions.

6. The flow path device according to claim 5, wherein an outer edge sealed portion, which is configured to extend in a manner so as to surround the non-sealed portions and join the first sheet and the second sheet to each other, is provided in the device main body.

7. The flow path device according to claim 1, wherein the flow path sealed portions comprise:
the plurality of first ports; and
the second port.

8. The flow path device according to claim 1, wherein the device main body further comprises:
a second portion that includes the filter accommodating chamber, the second portion being separated from the first portion to form an empty space between the first portion and the second portion.

9. The flow path device according to claim 8, wherein the second portion further comprises:
a third port at a first edge of the second portion that faces the second edge of the first portion, the third port being in communication with the filter accommodating chamber.

10. The flow path device according to claim 9, wherein the second portion further comprises:
a fourth port at a second edge of the second portion that is opposite the first edge of the second portion, the fourth port being in communication with the filter accommodating chamber.

11. The flow path device according to claim 9, wherein the device main body further comprises:
a connecting part that connects the second port of the first portion to the third port of the second portion.

12. The flow path device according to claim 11, wherein the empty space is at opposing sides of the connecting part.

13. The flow path device according to claim 11, wherein the empty space enables a clamp to attach to the connecting part.

14. A flow path device in which there are formed flow paths configured to allow at least one liquid of a biological fluid and a medicinal solution to flow therethrough, the flow path device comprising:
a device main body in which there are provided sealed portions configured to mutually join a plurality of sheets formed by a soft material in a liquid-tight manner to thereby form the flow paths in an interior of the sheets;
wherein the device main body comprises a first main body portion, a second main body portion, and a connecting part configured to connect the first main body portion and the second main body portion;
the first main body portion comprising:
a plurality of first flow paths;
a plurality of first ports at a first edge of the first main body portion and in communication with the plurality of first flow paths;
a second flow path in communication with the plurality of first flow paths; and
a second port in communication with the second flow path and at a second edge of the first main body portion opposite the first edge;
the second main body portion comprising:
a filter accommodating chamber provided in the second flow path and in which there is accommodated a filter member configured to remove a predetermined biological component in the biological fluid; and
a third flow path through which the liquid having passed through the filter accommodating chamber flows;
wherein the connecting part forms at least a portion of the second flow path between the second port and the second main body portion.

15. The flow path device according to claim 14, wherein spaces configured to separate the first main body portion and the second main body portion from each other are provided around a periphery of the connecting part.

16. A biological component bag system configured to collect a desired biological component from a biological fluid, the biological component bag system comprising:
a plurality of first bags in which the biological fluid is accommodated;

a flow path device to which the plurality of first bags are connected; and a second bag configured to accommodate the biological component which is guided from the plurality of first bags via the flow path device;

wherein the flow path device comprises a device main body configured to allow at least one liquid of the biological fluid and a medicinal solution to flow therethrough;

the device main body comprising:
 a first sheet formed by a soft material; and
 a second sheet formed by a soft material and that is superimposed on the first sheet;

wherein the device main body comprises a first portion including:
 a plurality of first flow paths;
 a plurality of first ports at a first edge of the first portion and in communication with the plurality of first flow paths;
 a second flow path configured to communicate with the plurality of first flow paths; and
 a second port in communication with the second flow path and at a second edge of the first portion opposite the first edge;

a filter accommodating chamber provided in the second flow path and in which there is accommodated a filter member configured to remove a predetermined biological component in the biological fluid; and a third flow path through which the liquid having passed through the filter accommodating chamber flows;

wherein flow path sealed portions, which are configured to join the first sheet and the second sheet to each other in a liquid-tight manner, are provided in the device main body.

17. The biological component bag system according to claim 16, further comprising a medicinal solution bag connected to the flow path device, and in which there is accommodated a medicinal solution to be added to the second bag via the flow path device.

18. The biological component bag system according to claim 17, wherein:
 a buffy coat as the biological fluid is accommodated in each of the plurality of first bags;
 a platelet additive solution as the medicinal solution is accommodated in the medicinal solution bag;
 the filter member of the flow path device removes leukocytes from the buffy coat; and
 blood platelets that have passed through the flow path device, and the platelet additive solution are accommodated in the second bag.

* * * * *